(12) United States Patent
Ginn et al.

(10) Patent No.: US 6,391,048 B1
(45) Date of Patent: *May 21, 2002

(54) INTEGRATED VASCULAR DEVICE WITH PUNCTURE SITE CLOSURE COMPONENT AND SEALANT AND METHODS OF USE

(75) Inventors: Richard S. Ginn; W. Martin Belef, both of San Jose, CA (US)

(73) Assignee: Integrated Vascular Systems, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/610,238

(22) Filed: Jul. 5, 2000

Related U.S. Application Data

(63) Continuation-in-part of application No. 09/478,179, filed on Jan. 5, 2000, now Pat. No. 6,197,042.

(51) Int. Cl.⁷ .............................................. A61B 17/04
(52) U.S. Cl. ..................... 606/213; 606/139; 606/219
(58) Field of Search ................................ 606/213, 219, 606/139

(56) References Cited

U.S. PATENT DOCUMENTS

| | | | |
|---|---|---|---|
| 3,586,002 A | 6/1971 | Wood | 606/153 |
| 3,604,425 A | 9/1971 | Le Roy | 128/325 |
| 3,757,629 A | 9/1973 | Schneider | 85/49 |
| 3,805,337 A | 4/1974 | Branstetter | 24/27 |
| 4,192,315 A | 3/1980 | Hilzinger et al. | 128/346 |
| 4,217,902 A | 8/1980 | March | 128/325 |
| 4,396,139 A | 8/1983 | Hall et al. | 227/19 |
| 4,485,816 A | 12/1984 | Krumme | 128/334 |
| 4,505,274 A | 3/1985 | Speelman | 606/153 |
| 4,586,503 A | 5/1986 | Kirsch et al. | 128/334 |
| 4,777,950 A | 10/1988 | Kees, Jr. | 128/325 |
| 4,860,746 A | 8/1989 | Yoon | 128/326 |
| 4,865,026 A | 9/1989 | Barrett | |
| 4,917,087 A | 4/1990 | Walsh et al. | 606/153 |
| 4,950,258 A | 8/1990 | Kawai et al. | 604/281 |
| 5,007,921 A | 4/1991 | Brown | 606/221 |
| 5,026,390 A | 6/1991 | Brown | 606/221 |
| 5,053,008 A | 10/1991 | Bajaj | 604/104 |
| 5,061,274 A | 10/1991 | Kensey | 606/213 |
| 5,108,420 A | 4/1992 | Marks | 606/213 |
| 5,156,609 A | 10/1992 | Nakao et al. | 606/142 |
| 5,176,648 A | 1/1993 | Holmes et al. | 604/164 |
| 5,192,302 A | 3/1993 | Kensey et al. | 606/213 |
| 5,222,974 A | 6/1993 | Kensey et al. | 606/213 |
| 5,304,184 A | 4/1994 | Hathaway et al. | 606/144 |
| 5,334,217 A | 8/1994 | Das | 606/213 |
| 5,366,458 A | 11/1994 | Korthoff et al. | 606/151 |
| 5,478,354 A | 12/1995 | Tovey et al. | 606/219 |
| 5,527,322 A | 6/1996 | Klein et al. | 606/144 |
| 5,674,231 A | 10/1997 | Green et al. | 606/142 |

(List continued on next page.)

FOREIGN PATENT DOCUMENTS

| WO | WO 97/20505 | 6/1997 | A61B/17/00 |
|---|---|---|---|
| WO | WO 98/24374 | 6/1998 | A61B/17/00 |
| WO | WO 99/62408 | 12/1999 | |
| WO | WO 00/07640 | 2/2000 | |
| WO | WO 00/56223 | 9/2000 | |
| WO | WO 00/56227 | 9/2000 | |

*Primary Examiner*—Gary Jackson
(74) *Attorney, Agent, or Firm*—Lyon & Lyon LLP

(57) ABSTRACT

Apparatus and methods are provided for use in sealing a vascular puncture site. The invention comprises an integrated vascular device having a sheath with a closure component and puncture sealant. The closure component is disposed on and advanceable over the exterior of the sheath and may comprise any of a variety of apparatus suited for closing a vascular puncture. Once the closure component has been actuated to close the puncture, sealant is introduced to seal the puncture. The sheath and closure component are then removed from the patient.

29 Claims, 5 Drawing Sheets

U.S. PATENT DOCUMENTS

| | | |
|---|---|---|
| 5,683,405 A | 11/1997 | Yacoubian et al. ......... 606/158 |
| 5,695,505 A | 12/1997 | Yoon ........................... 606/157 |
| 5,782,844 A | 7/1998 | Yoon et al. .................. 606/139 |
| 5,782,861 A | 7/1998 | Cragg et al. ................. 606/216 |
| 5,810,846 A | 9/1998 | Virnich et al. .............. 606/142 |
| 5,810,851 A | 9/1998 | Yoon ........................... 606/148 |
| 5,817,113 A * | 10/1998 | Gifford, III et al. ........ 606/213 |
| 5,820,631 A * | 10/1998 | Nobles ........................ 606/213 |
| 5,830,125 A | 11/1998 | Scribner et al. ............ 606/139 |
| 5,879,366 A | 3/1999 | Shaw et al. |
| 5,910,155 A | 6/1999 | Ratcliff et al. .............. 606/213 |
| 5,964,782 A * | 10/1999 | LaFontaine et al. ........ 606/213 |
| 5,984,934 A | 11/1999 | Ashby et al. ............... 606/151 |
| 6,007,563 A | 12/1999 | Nash et al. .................. 606/213 |
| 6,036,720 A | 3/2000 | Abrams et al. ............. 606/213 |
| 6,063,085 A | 5/2000 | Tay et al. ..................... 606/50 |
| 6,077,281 A | 6/2000 | Das ............................. 606/151 |
| 6,077,291 A | 6/2000 | Das ............................. 606/213 |
| 6,080,182 A | 6/2000 | Shaw .......................... 606/213 |
| 6,080,183 A | 6/2000 | Tsugita et al. .............. 606/213 |
| 6,120,524 A * | 9/2000 | Taheri ......................... 606/213 |

* cited by examiner

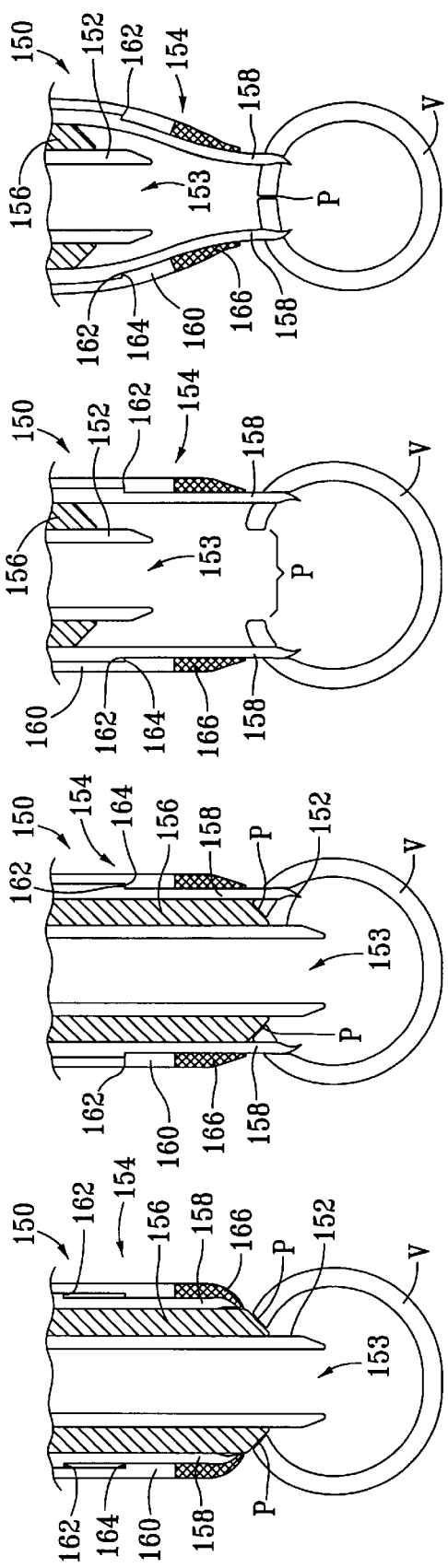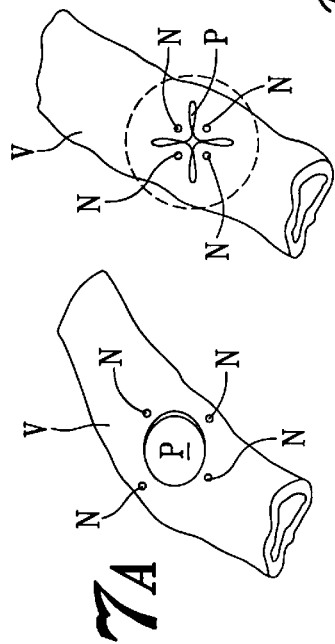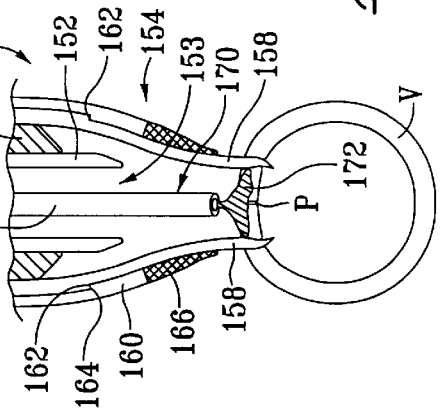

INTEGRATED VASCULAR DEVICE WITH PUNCTURE SITE CLOSURE COMPONENT AND SEALANT AND METHODS OF USE

REFERENCE TO RELATED APPLICATION

This application is a continuation-in-part of U.S. patent application Ser. No. 09/478,179 filed Jan. 5, 2000 now U.S. Pat. No. 6,197,042.

FIELD OF THE INVENTION

The present invention relates to apparatus and methods for sealing an iatrogenic puncture in a vessel formed in conjunction with a diagnostic or therapeutic treatment. More particularly, the present invention provides an integrated vascular device comprising a sheath having a puncture closure component and puncture sealant.

BACKGROUND TO THE INVENTION

Catheterization and interventional procedures, such as angioplasty and stenting, generally are performed by inserting a hollow needle through a patient's skin and muscle tissue into the vascular system. A guide wire is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurse's time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al. describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel and issues of biocompatibility.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art, Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, devices employing resilient or deformable clips have been developed. U.S. Pat. No. 5,478,354 to Tovey et al. describes the use of resilient clips in conjunction with a trocar to close abdominal puncture wounds. U.S. Pat. No. 5,810,846 to Virnich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft having a distal end formed with one or more opposed pairs of resilient grasping prongs and that is advanced over a guide wire through a coaxial hollow tube to a position at the distal end of the tube just proximal of the puncture. The grasping prongs are extended beyond the distal end of the tube to grasp the vessel on opposing sides of the puncture. The shaft then is partially retracted, causing the prongs to contract within the tube, thereby sealing the puncture site.

The use of backbleed indication as a positioning technique within a vascular puncture is known. For example, U.S. Pat. No. 4,317,445 to Robinson describes a flashback chamber for providing visual indication of venous entry of a cannula. However, that device does not discuss vascular wound closure. U.S. Pat. No. 5,676,689 to Kensey et al., which claims priority from the U.S. Pat. No. 5,222,974 discussed above, uses a vessel location device to simplify positioning of the biodegradable plug. The vessel locator enables blood from the vessel to flow there through so that the position of the vessel may be determined. However, the Kensey system only proffers one closure device, and that device is complex and raises concerns about biocompatibility. It also requires the closure component to be positioned within the puncture, thereby increasing the likelihood of dangerous over-advancement of the plug into the vessel.

The percutaneous puncture closure devices described in the foregoing patents generally have the drawback that they require relatively complex mechanisms and require time consuming manipulation to achieve hemostasis. It therefore would be desirable to provide apparatus and methods suitable for vascular puncture closure that overcome these disadvantages of previously known devices.

It also would be desirable to provide apparatus and methods that quickly and effectively achieve hemostasis.

It further would be desirable to provide apparatus and methods wherein all foreign materials left in a patient's body are bioabsorbable.

It still further would be desirable to provide vascular puncture closure apparatus and methods that are safe, low cost, and easy to use.

SUMMARY OF THE INVENTION

In view of the foregoing, it is an object of the present invention to provide vascular puncture closure apparatus and methods that overcome disadvantages of previously known devices.

It also is an object of this invention to provide apparatus and methods suitable for vascular puncture closure that quickly and effectively achieve hemostasis.

It further is an object of the present invention to provide apparatus and methods wherein all foreign materials left in a patient's body are bioabsorbable.

It still further is an object of the present invention to provide vascular puncture closure apparatus and methods that are safe, low cost, and easy to use.

These and other objects of the present invention are accomplished by providing an integrated vascular device comprising a sheath having a puncture closure component and puncture sealant. The closure component is disposed on and advanceable over the exterior of the sheath, which may, for example, comprise an introducer sheath, a trocar, or a catheter. The closure component may comprise any of a variety of apparatus suited to close a vascular puncture. Once the closure component has been actuated to close the puncture, sealant is introduced to the exterior surface of the closed puncture, preferably through the sheath's interior lumen, where the sealant seals the puncture closed. The sheath with closure component is then removed from the patient.

In a preferred embodiment constructed in accordance with the present invention, the closure component comprises a twist closure device. The device pierces tissue surrounding the vascular puncture and then is rotated to close the wound. In an alternative embodiment, the closure component comprises needles and an elastic segment surrounding the needles. The needles pierce the puncture with the elastic segment expanded. The segment is then allowed to resiliently contract to an unstressed configuration of smaller diameter, thereby drawing the needles together and closing the wound.

In a still further alternative embodiment, the needles, or prongs, are elastically deformed to an expanded diameter, in which they pierce the tissue adjacent to puncture. The needles then are allowed to resiliently contract to an unstressed configuration of smaller diameter, thereby closing the wound.

Sealant then may be introduced, preferably through the interior lumen of the sheath, to seal the puncture closed. The sealant may comprise any of a variety of sealants, per se known, including adhesives, sutures, and clips, all of which are preferably bioabsorbable. Alternatively, the closure component may further comprise the sealant, wherein the closure component is left in place within the vessel until hemostasis naturally occurs, or wherein the closure component comprises a monopolar electrode or opposed bipolar electrodes that cauterize the wound with RF current. In addition to cauterization, RF energy generates heat that beneficially causes shrinkage of the vascular tissue, thereby assisting closure of the wound. Thermal energy from electrical induction, infrared light, ultrasonic vibration, microwave or laser irradiation, and other means may also be used to seal the puncture.

Advantageously, the puncture closure component of the present invention is inexpensively integrated into a sheath, thereby minimizing mechanical complexity while providing quick, safe, effective, and easy-to-use apparatus for achieving vascular closure that overcomes drawbacks of previously known devices. Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 6A–6E are side-sectional views of a further alternative embodiment in use at a vascular puncture site, illustrating a method of sealing the puncture site; and FIGS. 7A and 7B are isometric views of a section of vessel including and corresponding to the vascular puncture site of FIG. 6, further illustrating the method of FIG. 6.

DETAILED DESCRIPTION OF THE INVENTION

The integrated vascular sheath with closure component of the present invention overcomes disadvantages associated with previously known methods and apparatus for sealing a vascular puncture by providing a quick, simple, safe, low cost, effective, and easy-to-use solution to wound closure. Apparatus constructed in accordance with the present invention provide vascular access and wound closure in a single device, eliminating the time and manipulation required to insert a separate closure device at the completion of a procedure.

Figure 1:
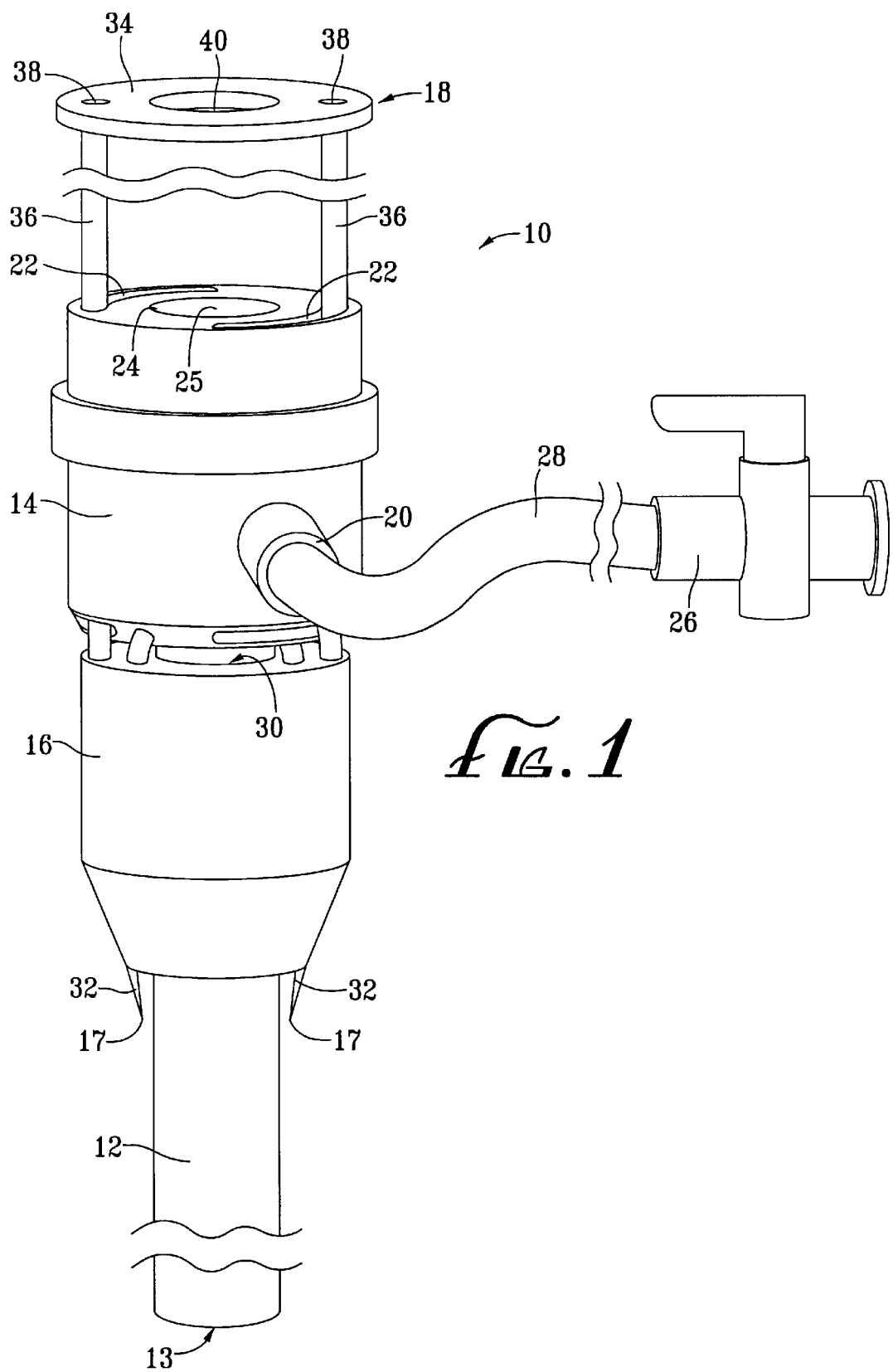
FIG. 1 is a side view of a preferred embodiment of an integrated vascular device constructed in accordance with the present invention.

Referring to FIG. 1, a first embodiment of apparatus of the present invention is described. Vascular device 10 comprises sheath 12 coupled to hub 14, closure component 16, and closure actuator 18.

Sheath 12, which may, for example, comprise an introducer sheath, a trocar, or a catheter, includes central lumen 13 through which other devices may be introduced into the vasculature, for example, to perform a diagnostic or interventional procedure such as angiography, angioplasty, or stenting, or to seal a puncture site.

Hub 14 is mounted on the proximal end of sheath 12 and includes side port 20, arc lumens 22, and device port 24. Device port 24 communicates with central lumen 13 of sheath 12, and has self-sealing elastomeric membrane 25 disposed across it. Self-sealing membrane 25, which may comprise, for example, latex or a biocompatible synthetic rubber, permits interventional devices to be introduced through device port 24, while preventing blood loss through central lumen 13. Side port 20 of hub 14 is also in communication with central lumen 13, and is connected to hemostatic port 26 via biocompatible tubing 28.

In accordance with the principles of the present invention, closure component 16 comprises lumen 30 that receives sheath 12. Component 16 is slidably disposed on the exterior of sheath 12 and is movable from a stowed position, adjacent hub 14, to a distal deployment position, where tines 17 of component 16 are urged into engagement with tissue surrounding a vascular puncture. Closure component 16 comprises at least two sharpened tips, or tines 17. Tines 17 preferably comprise backbleed ports 32. Closure component 16 is rotatable within arc-lumens 22 about the longitudinal axis of sheath 12, so that, with tines 17 engaging tissue surrounding the vascular puncture, component 16 closes the puncture.

Closure actuator 18 comprises plunger 34 and tubes 36, which are configured to slidably pass through arc lumens 22 of hub 14. The proximal ends of tubes 36 are coupled to backbleed bores 38 of plunger 34. The distal ends of tubes 36 are mounted, either permanently or detachably, in closure component 16, so that movement of plunger 34 causes corresponding proximal or distal movement of closure component 16. Likewise, rotation of plunger 34 causes corresponding rotation of tubes 36 within arc lumens 22, which, in turn, rotates closure component 16 about the longitudinal axis of sheath 12.

Plunger 34 further comprises device bore 40, coaxially aligned with device port 24, and through which interventional devices or puncture sealants may be passed. As described in detail hereinafter, when plunger 34 is moved to its proximal-most position, closure component 16 is disposed adjacent to hub 14 and preferably provides adequate clearance for interventional devices to be inserted through device port 24 and central lumen 13 into the patient's vasculature. When moved to its distal-most position, plunger 34 causes tubes 36 to urge closure component 16 distally. Interventional devices or sealants then may be introduced through device bore 40, device port 24, and central lumen 13 into the vasculature.

Backbleed bores 38 of plunger 32 are in communication with backbleed lumens (not shown) within tubes 36. The backbleed lumens of tubes 36 are in communication with backbleed ports 32 of tines 17, thereby establishing a complete backbleed path through ports 32, the lumens (not shown) of tubes 36, and bores 38. When tines 17 of closure component 16 pierce a vessel wall surrounding a vascular puncture, blood enters backbleed ports 32 and exits through backbleed bores 38, providing visual confirmation to a surgeon that tines 17 are positioned within the vessel wall. The backbleed path thus enables the surgeon to determine when closure component 16 has been sufficiently advanced to permit rotation of component 16 to close the puncture, while reducing the risk that component 16 is either short of the puncture site or is extended into the vessel.

In conjunction with closure of the puncture site caused by rotation of component 16, a puncture sealant may be introduced to the puncture site to seal the site closed. The sealant may, for example, comprise an adhesive, such as a bioglue, tissue sealant, or clotting agent, delivered through hemostatic port 26, biocompatible tubing 28, side port 20 and central lumen 13 of introducer sheath 12 to the vascular puncture to further help seal the vessel after puncture closure with closure component 16. Alternatively, the adhesive may be delivered through device port 24 or through the backbleed path described above. Instead of adhesives, the closure component may further comprise the sealant, wherein the closure component is left in place within the vessel until hemostasis naturally occurs. The sealant may also comprise sutures delivered through central lumen 13. Additionally, the sealant may comprise thermal energy application from, for example, electrical induction, infrared light, ultrasonic vibration, microwave or laser irradiation, and other means.

Figure 2:
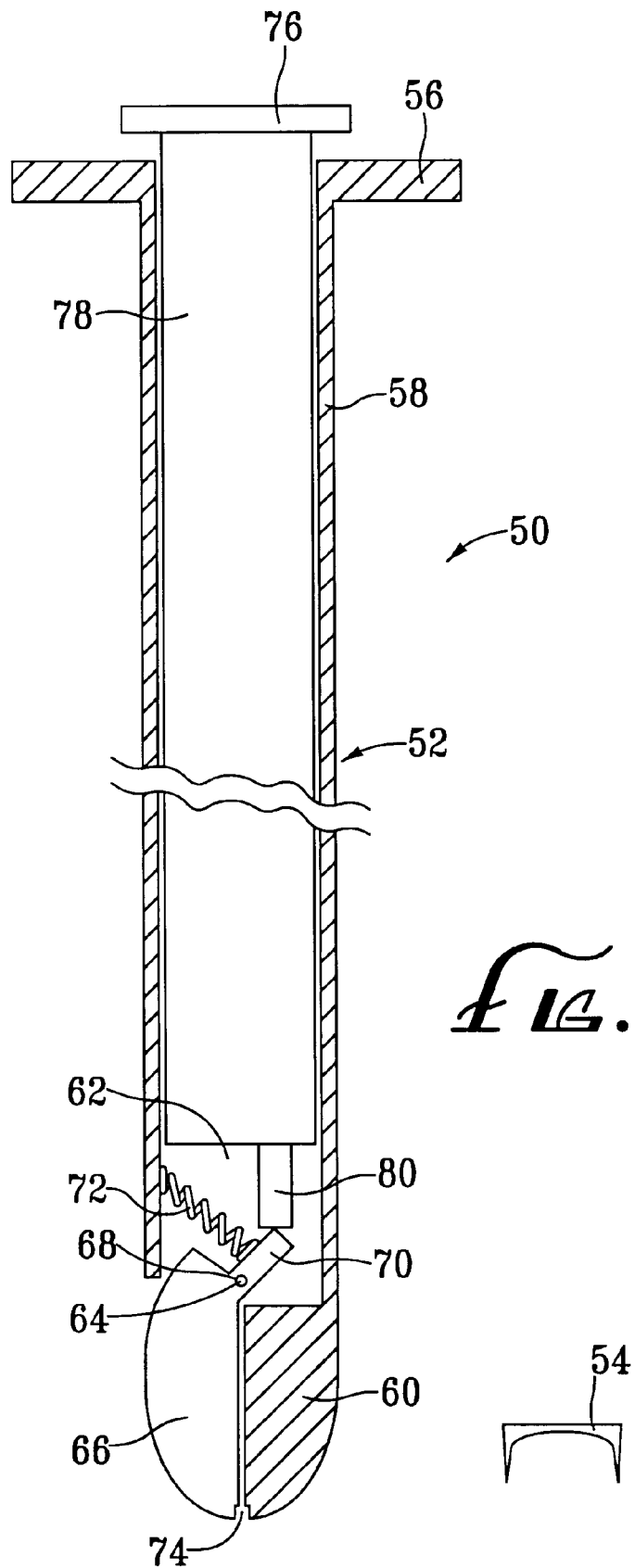
FIG. 2 is a side-sectional view of a sealing device for use with the vascular device of FIG. 1.

With reference to FIG. 2, an alternative puncture sealing device in accordance with the present invention is described. Sealing device 50 comprises delivery device 52 and clip 54. Delivery device 52 comprises proximal end 56 attached to tube 58. Tube 58 terminates at first jaw 60 at its distal end and further comprises lumen 62 and pin 64. Pin 64 extends into lumen 62 from an interior surface of tube 58 and is disposed perpendicular to the longitudinal axis of tube 58.

Delivery device 52 further comprises second jaw 66 having female connector 68 coupled to pin 64, so that second jaw 66 pivots about pin 64. Second jaw 66 further comprises moment arm 70. Tension spring 72 is coupled to moment arm 70 and to the interior surface of tube 58 in a manner that biases second jaw 66 against first jaw 60.

First jaw 60 and second jaw 66 preferably form channel 74 when biased against one another. Channel 74 is configured to receive clip 54. The biasing force applied by tension spring 72 holds clip 54 within channel 74, so that the clip may be advanced into tissue surrounding a vascular puncture that has had its edges approximated by closure component 16.

Delivery device 52 still further comprises plunger 76 coupled to pushrod 78 having release arm 80. Pushrod 78 is received within lumen 62 of tube 58, so that release arm 80 engages moment arm 70.

Distal advancement of pushrod 78, via application of force to plunger 76, causes release arm 80 to urge moment arm 70 distally. This motion overcomes the biasing force applied by tension spring 72 and causes second jaw 66 to pivot about pin 64. Second jaw 66 thus no longer contacts first jaw 60, and clip 54 is released from channel 74. Tube 58, first jaw 60, second jaw 66, and clip 54 of sealing device 50 preferably are sized for introduction into a patient's vasculature through device bore 40, device port 24, and lumen 13 of vascular device 10.

Referring to FIGS. 3A–3D through 4A–4D, in conjunction with FIGS. 1 and 2, a method of using vascular device 10 with sealing device 50 is described. Sheath 12 is advanced through skin, fat, and muscle tissue into vessel V, through the vessel wall tissue surrounding vascular puncture P. With plunger 34 and tubes 36 of actuator 18 in the proximal-most, fully retracted position, an interventional procedure is performed by introducing one or more interventional devices, e.g. angioplasty balloons, stent delivery systems, atherectomy devices, etc., through device port 24 and lumen 13 of sheath 12, in accordance with well-known techniques. Side port 20 may be used to infuse fluids, e.g., contrast agents or medications, into the vessel through sheath 12 during the interventional procedure.

Upon completion of the procedure, vascular device 10 may be advantageously used to close vascular puncture P. At this point, closure actuator 18 and closure component 16 are disposed in the proximal-most position, with component 16 adjacent to hub 14. Closure actuator 18 is advanced by urging plunger 34 in the distal direction, thus causing tubes 36 to slide through arc lumens 22 of hub 14 and advance closure component 16.

Figure 3A:
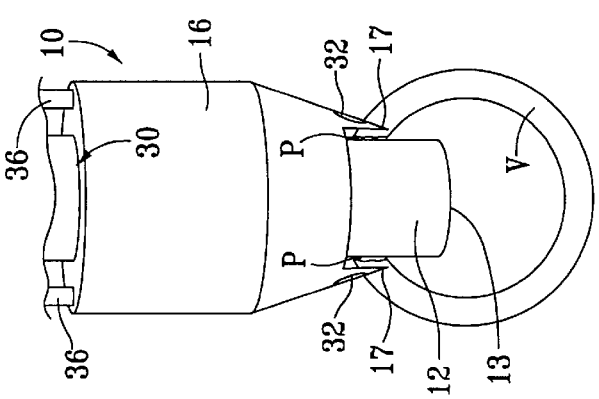
FIGS. 3A–3D are side views of the closure component of FIG. 1 in use at a vascular puncture site, shown in section, with the sealing device of FIG. 2, illustrating a method of sealing the puncture site.
Figure 4A:
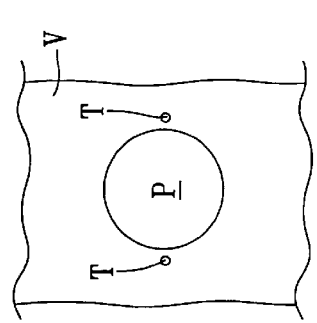
FIGS. 4A–4D are top views of the vascular puncture site of FIG. 3, corresponding to the side-sectional views of FIG. 3, further illustrating the method of FIG. 3.

As seen in FIG. 3A, continued distal advancement of plunger 34 causes tines 17 at the distal end of closure component 16 to pierce tissue surrounding puncture P, so that the backbleed ports 32 of tines 17 directly communicate with the puncture wound. Tine punctures T in FIG. 4A represent the points at which tines 17 enter vessel V. The presence of pressure in the vessel higher than atmospheric pressure causes blood to pass through backbleed ports 32, through the backbleed lumens (not shown) of tubes 36, and exit through the proximal ends of backbleed bores 38, thus confirming that tines 17 have engaged tissue around the puncture site and should not be advanced further.

Figure 3B:
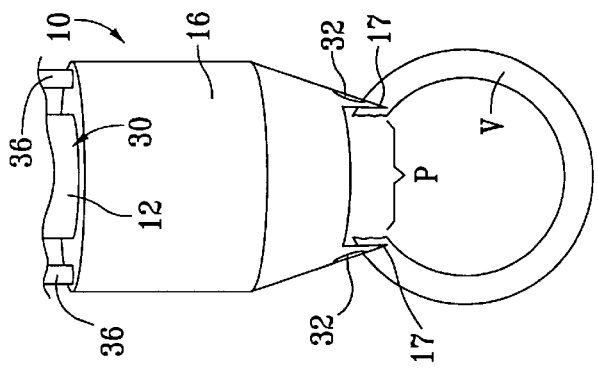
Figure 4B:
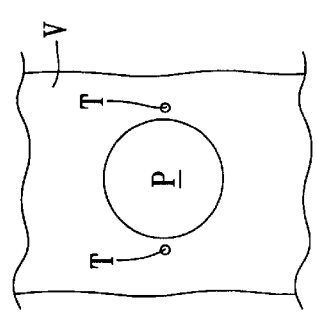
Figure 3C:
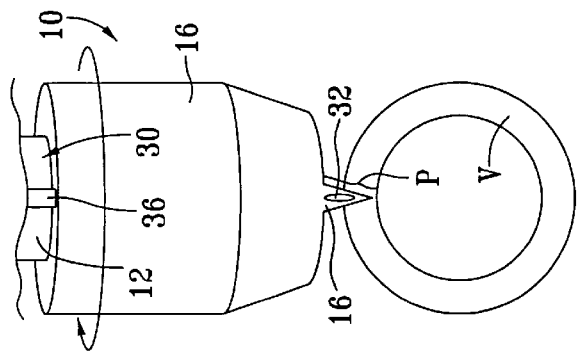
Figure 4C:
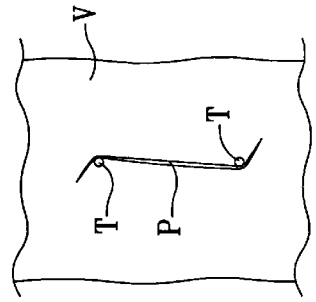

In FIG. 3B, sheath 12 is removed from puncture P to facilitate closure of the puncture. Closure actuator 18 is held stationary while hub 14 is withdrawn proximally, thereby withdrawing sheath 12 proximally from puncture P. The puncture remains open, as seen in FIG. 4B. With sheath 12 no longer within puncture P, closure actuator 18 is rotated within arc lumens 22 to rotate closure component 16. Rotation of closure component 16 causes tines 17 to rotate and urge the puncture closed, as seen in FIGS. 3C and 4C.

Upon closure of puncture P, a sealant is introduced to seal the wound closed. The sealant may, for example, comprise an adhesive, such as a bioglue, tissue sealant, or clotting agent, it may comprise a suture, it may comprise thermal energy application, or it may comprise leaving the closure component in place within vessel V until hemostasis naturally occurs. Alternatively, the sealing device may comprise a clip, as described hereinafter.

Figure 3D:
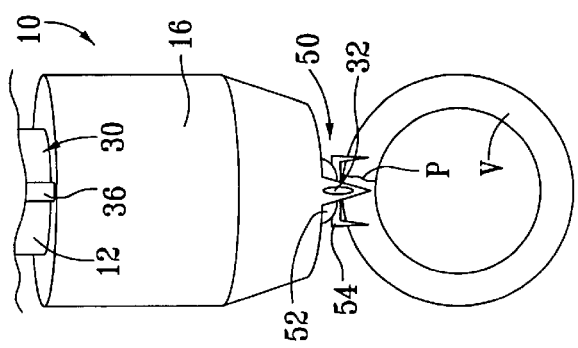
Figure 4D:
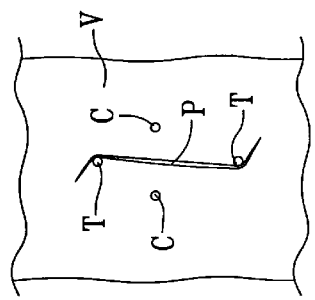

FIGS. 3D and 4D show apparatus 10 used in conjunction with sealing device 50 of FIG. 2. With clip 54 disposed in channel 74 of delivery device 52, the delivery device is delivered to vessel V through device bore 40 of closure actuator 18, device port 24 of hub 14, and central lumen 13 of sheath 12. Clip 54 punctures the vessel at tissue surrounding closed puncture P, creating clip punctures C and sealing the puncture. Pushrod 78 of delivery device 52 is then actuated to separate second jaw 66 from first jaw 60 to release clip 54 from delivery device 52. Apparatus 10 and delivery device 52 are removed from the patient to complete the procedure. Clip 54 maintains closure until hemostasis occurs and is preferably bioabsorbable so that no foreign materials are permanently implanted in the patient's body. Additional clips may also be implanted, as required.

Figures 5A, 5B, 5C:
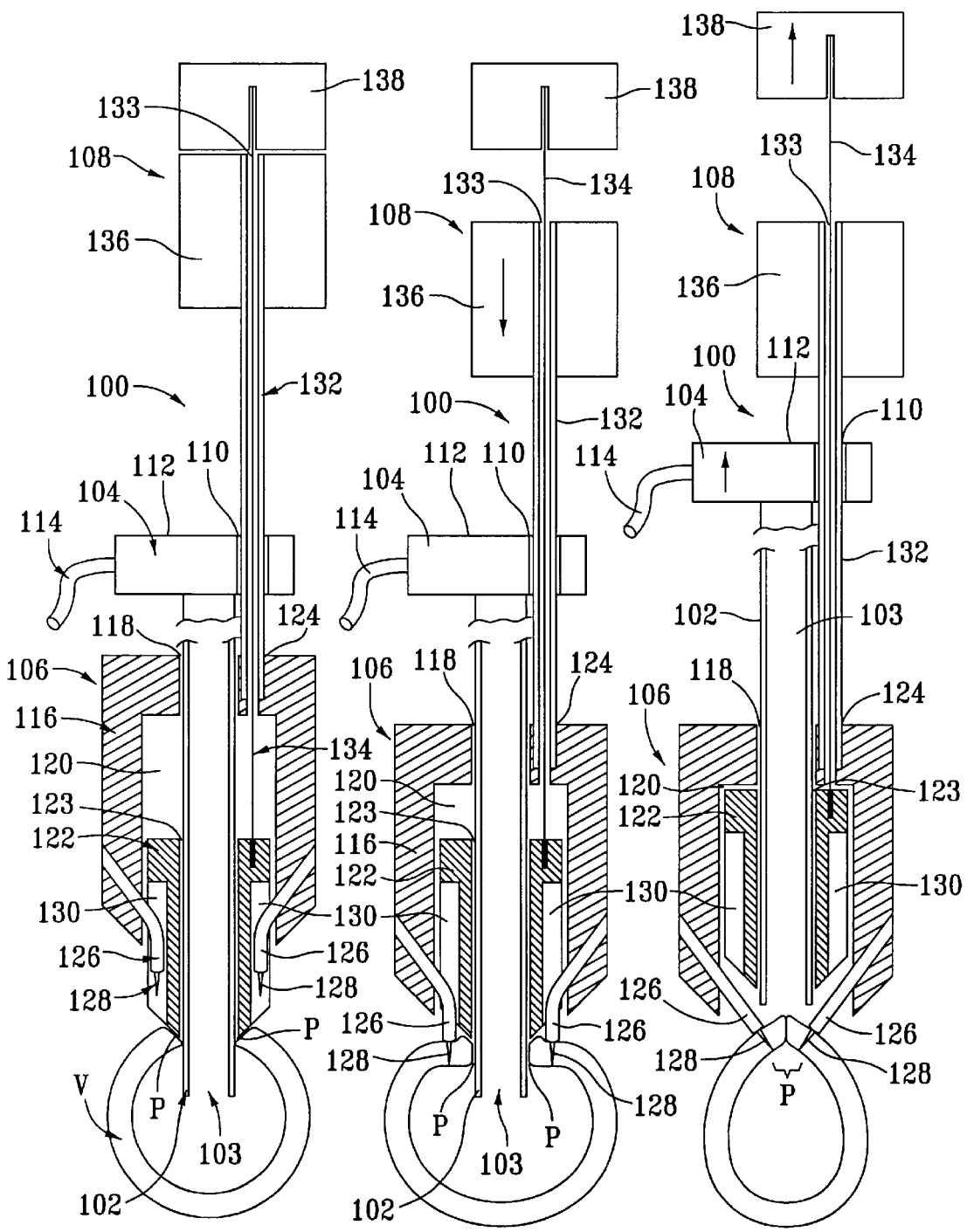
FIGS. 5A–5C are side-sectional views of an alternative embodiment of an integrated vascular device of the present invention in use at a vascular puncture site, illustrating a method of sealing the puncture site.

With reference now to FIGS. 5A–5C, an alternative integrated vascular device in accordance with the present invention is described. Apparatus 100 comprises sheath 102 coupled to hub 104, closure component 106, and closure actuator 108.

Like sheath 12, sheath 102 may, for example, comprise an introducer sheath, a trocar, or a catheter, and includes central lumen 103 through which other devices may be introduced into the vasculature, for example, to perform a diagnostic or interventional procedure such as angiography, angioplasty, or stenting, or to seal a puncture site. Hub 104 comprises bore 110, which slidably receives actuator 108, and device port 112, which is in communication with central lumen 103 of sheath 102 and permits introduction of interventional devices while preventing blood loss through central lumen 103. Hub 104 further comprises side port 114.

Closure component 106 comprises outer housing 116 having lumen 118 configured to slidably receive sheath 102, bore 120 for slidably receiving inner housing 122, lumen 124 adapted to receive closure actuator 108, and needles or prongs 126 with sharpened tips 128. Inner housing 122 has lumen 123 adapted to receive sheath 102 and channels 130 adapted to receive prongs 126. Component 106 comprises at least two prongs 126, and preferably comprises four.

Closure actuator 108 comprises actuation tube 132 having lumen 133, actuation rod 134 disposed within actuation tube 132, first plunger 136 coupled to the proximal end of tube 132, and second plunger 138 coupled to the proximal end of rod 134. The distal end of tube 132 is affixed, either permanently or detachably, in lumen 124 to outer housing 116 of closure component 106, while the distal end of rod 134 is coupled to inner housing 122.

To perform an interventional procedure through central lumen 103 of sheath 102, the sheath is advanced through skin, fat, and muscle tissue into vessel V, through vascular puncture P, in accordance with well-known techniques. With closure component 106 in the proximal-most, fully retracted position adjacent hub 104, the interventional procedure then is performed by introducing one or more interventional devices, e.g. angioplasty balloons, stent delivery systems, atherectomy devices, etc., through device port 112 and lumen 103 of sheath 102, again in accordance with well-known techniques. Side port 114 may be used to infuse fluids, e.g., contrast agents or medications, into the vessel through sheath 102 during the interventional procedure.

Upon completion of the procedure, apparatus 100 advantageously may be used to close the vessel. Closure component 106 is advanced distally by urging plungers 136 and 138 distally. Inner housing 122 is only partially received within bore 120 of outer housing 116 so that prongs 126 are elastically deformed and received within channels 130. As shown in FIG. 5A, closure component 106 is advanced until inner housing 122 abuts against the vessel V, as may be determined, for example, with a backbleed indicator (not shown).

In FIG. 5B, first plunger 136 is urged distally to distally advance actuation tube 132 and outer housing 116, while second plunger 138 and sheath 102 are held stationary. Advancement of outer housing 116 advances sharpened tips 128 of prongs 126 into tissue surrounding puncture P.

In FIG. 5C, sheath 102 and second plunger 138 are retracted proximally to draw sheath 102 out of vessel V and to draw inner housing 122 completely within bore 120 of outer housing 116. Proximally retracting inner housing 122 via actuation rod 134 and second plunger 138 removes prongs 126 of outer housing 116 from channels 130 of the inner housing. The prongs resiliently contract to a lower stress configuration, thereby drawing opposing sides of puncture P together and closing the wound. A sealant, for example clip 54 of FIG. 2, may then be introduced to the closed puncture to seal the site closed, as discussed hereinabove. Alternatively, the sealing device may comprise RF current, supplied by an RF generator (not shown), applied across opposed tips 128, which act as bipolar electrodes.

Referring to FIGS. 6A–6E, as well as FIGS. 7A and 7B, a still further alternative embodiment of apparatus of the present invention is described. FIGS. 6 depict the closure component of an integrated vascular device in use at vascular puncture P within vessel V. Apparatus 150 comprises sheath 152 coupled to a hub (not shown), closure component 154, and a closure actuator (not shown). Various closure actuators for use with closure component 154 will be apparent to those of skill in the art from the foregoing embodiments.

Sheath 152 may, for example, comprise an introducer sheath, a trocar, or a catheter, and includes central lumen 153 through which other devices may be introduced into the vasculature, for example, to perform a diagnostic or interventional procedure such as angiography, angioplasty, or stenting, or to seal a puncture site. Closure component 154 comprises spacer 156, needles 158, and needle cover 160. Spacer 156 is coaxially and slidably disposed about the exterior of sheath 152, and preferably has an annular diameter of about 1 mm to ensure that needles 158 engage the tissue surrounding puncture P rather than enter the puncture, so that the needles are able to draw the wound closed, as described hereinbelow. Needles 158 are disposed between spacer 156 and cover 160 during advancement to puncture P. Needles 158 comprise ledges 162, which act as positive stops to prevent excessive advancement of the needles with respect to cover 160, which comprises corresponding annular ledge 164. Cover 160 further comprises elastic segment 166, configured to elastically deform needles 158. Closure component 154 comprises at least two needles 158, and preferably comprises four. Needles 158 may further comprise retaining means (not shown), such as barbs or hooks, to assist in gripping tissue.

As shown in FIG. 6A, sheath 152 may be advanced through skin, fat, and muscle tissue into vessel V, through vascular puncture P, in accordance with well-known techniques. With closure component 154 in a proximal-most, fully retracted position adjacent the hub, an interventional procedure is performed through central lumen 153 of sheath 152 by introducing one or more interventional devices through the lumen into the patient's vasculature. Closure component 154 then is advanced via the closure actuator until it abuts against vessel V, as may be determined, for example, with a backbleed indicator, such as described for the foregoing embodiments. Cover 160 protects needles 158 and prevents snagging of tissue as closure component 154 is distally advanced down sheath 152 and through skin, fat, and muscle tissue. Spacer 156 retains needles 158 in a position away from the edge of puncture P.

In FIG. 6B, needles 158 are distally advanced with respect to needle cover 160 until ledge 162 abuts ledge 164. Needles 158 deflect elastic segment 166 of cover 160 outward and pierce tissue surrounding puncture P. FIG. 7A depicts, in isometric view, the segment of vessel V surrounding puncture P. With a needle arrangement comprising four needles 158, the needles create needle punctures N surrounding vascular puncture P. Sheath 152 and spacer 156 then are retracted proximally and removed from vessel V, as shown in FIG. 6C. As depicted in FIGS. 6D and 7B, elastic segment 166 of needle cover 160 resiliently contracts, thereby drawing needles 158 together and approximating the edges of the wound.

A sealant, such as a bioglue, tissue sealant, or clotting agent, then may be introduced to the puncture site to seal the wound closed. Alternatively, closure component 154 may be maintained in position until hemostasis occurs naturally, or sutures may be introduced through central lumen 153. In addition, or in the alternative, RF energy may be applied across needles 158, as described hereinabove with respect to FIG. 5, or a clip, such as clip 54 of sealing device 50 of FIG. 2, may be applied. Thermal energy from electrical induction, infrared light, ultrasonic vibration, microwave or laser irradiation, and other means may also be used to seal the puncture.

Illustratively, FIG. 6E depicts sealing device 170, comprising adhesive 172, being delivered through central lumen 153 within delivery sheath 174. After sufficient time for adhesive 172 to set, apparatus 150 is removed from vessel V.

Although preferred illustrative embodiments of the present invention are described hereinabove, it will be evident to one skilled in the art that various changes and modifications may be made without departing from the invention. It is intended in the appended claims to cover all such changes and modifications that fall within the true spirit and scope of the invention.

What is claimed is:

1. Apparatus for approximating opposing edges of a puncture in a vessel wall comprising:
   a tubular member having proximal and distal regions and an exterior surface;
   a closure component comprising at least two sharpened tips for engagement of the vessel wall, the closure component slidably disposed about the exterior surface of the tubular member, the closure component adapted to close the puncture;
   a closure actuator coupled to the closure component, the closure actuator adapted to advance the closure component from a region on the tubular member proximal of the puncture to the vessel wall, the closure actuator further adapted to the urge the closure component into engagement with the vessel wall and close the puncture; and
   at least one backbleed indicator port coupled to a proximal end of the tubular member to indicate a position of the closure component relative to the puncture.

2. The apparatus of claim 1, wherein the closure component further comprises at least two resilient prongs, the sharpened tips disposed on the distal ends of the prongs.

3. The apparatus of claim 2, wherein the prongs have an expanded delivery configuration configured for engagement of the vessel wall in a vicinity of the puncture, and a deployed configuration, wherein the prongs resiliently retract to close the puncture.

4. The apparatus of claim 1, wherein the closure component further comprises retaining means attached to the sharpened tips.

5. The apparatus of claim 1, wherein the closure actuator is adapted to rotate the closure component about a longitudinal axis of the tubular member to close the puncture.

6. The apparatus of claim 1, wherein the closure actuator comprises at least one elongated member coupled to the closure component.

7. The apparatus of claim 1 further comprising means for sealing the puncture, selected from a group consisting of RF energy, thermal energy application, electrical induction, infrared light, ultrasonic vibration, microwave or laser irradiation, clips, sutures, and adhesives.

8. The apparatus of claim 7, wherein the adhesives are selected from a group consisting of bioglues, tissue sealants, and clotting agents.

9. The apparatus of claim 7, wherein the means for sealing are bioabsorbable.

10. The apparatus of claim 1, wherein the sealant may be delivered through a lumen of the tubular member.

11. The apparatus of claim 1, wherein the tubular member is chosen from the group consisting of introducer sheaths, trocars, and catheters.

12. The apparatus of claim 1, wherein the closure actuator is detachably coupled to the closure component.

13. Apparatus for approximating opposing edges of a puncture in a vessel wall comprising:
   a tubular member having proximal and distal regions and an exterior surface;
   a closure component comprising at least two sharpened tips for engagement of the vessel wall, the closure component slidably disposed about the exterior surface of the tubular member, the closure component adapted to close the puncture; and
   a closure actuator coupled to the closure component, the closure actuator adapted to advance the closure component from a region on the tubular member proximal of the puncture to the vessel wall, the closure actuator further adapted to urge the closure component into engagement with the vessel wall and close the puncture; and
   a side port for introducing fluids into the tubular member.

14. The apparatus of claim 13, wherein the sealant may be delivered through the side port to the vessel wall in a vicinity of the puncture.

15. Apparatus for approximating opposing edges of a puncture in a vessel wall comprising:
   a tubular member having proximal and distal regions and an exterior surface;

a closure component comprising at least two sharpened tips for engagement of the vessel wall, the closure component slidably disposed about the exterior surface of the tubular member, the closure component adapted to close the puncture; and a closure actuator coupled to the closure component, the closure actuator adapted to advance the closure component from a region on the tubular member proximal of the puncture to the vessel wall, the closure actuator further adapted to urge the closure component into engagement with the vessel wall and close the puncture;

wherein the closure component further comprises a spacer, a needle cover disposed coaxially about the spacer, and at least two needles disposed therebetween, the sharpened tips disposed on distal ends of the needles.

16. The apparatus of claim 15, wherein the needle cover further comprises an elastic segment adapted to deform the needles from a delivery configuration configured for engagement of the vessel wall in a vicinity of the puncture, to a deployed configuration configured to draw opposing sides of the puncture together and close the puncture.

17. The apparatus of claim 16, wherein the elastic segment and a distal portion of the needles are positioned distal of the spacer in the deployed configuration.

18. A method of approximating opposing edges of a puncture in a vessel wall, the method comprising:

providing appartus comprising a tubular member having proximal and distal regions and a lumen extending therebetween, and a closure component slidably disposed on the tubular member, the closure component comprising a backbleed indicator port coupled to the proximal region of the tubular member;

inserting the distal region of the tubular member through a patient's skin into a vessel via the puncture;

performing an interventional or diagnostic procedure by advancing a device through the lumen of the tubular member;

advancing the closure component until blood from the puncture flows through the backbleed indicator port to the proximal region of the tubular member;

advancing the closure component through the skin until the component pierces the vessel wall on opposing sides of the puncture; and closing the puncture with the closure component.

19. The method of claim 18, wherein the apparatus further comprises a closure actuator that may be coupled to the closure component, and advancing the closure component through the skin comprises advancing the closure component through the skin with the closure actuator.

20. The method of claim 19, wherein the tubular member further comprises a hub having a lumen and the closure actuator further comprises an elongated member, wherein coupling the closure actuator to the closure component further comprises inserting the elongated member through the lumen of the hub.

21. The method of claim 18 further comprising removing the tubular member and closure component from the patient.

22. The method of claim 18 further comprising sealing the puncture closed.

23. The method of claim 22, wherein sealing the puncture closed comprises applying RF current to the closed puncture.

24. The method of claim 22, wherein sealing the puncture closed comprises delivering adhesive to the vessel wall in a vicinity of the puncture.

25. The method of claim 22, wherein sealing the puncture closed comprises piercing the vessel wall with a clip in a vicinity of the puncture.

26. The method of claim 22, wherein sealing the puncture closed comprises suturing the vessel wall closed with sutures.

27. The method of claim 22, wherein sealing the puncture closed comprises holding the puncture closed with the closure component until hemostasis occurs.

28. The method of claim 22, wherein sealing the puncture closed comprises applying thermal energy to the puncture.

29. The method of claim 18, wherein closing the puncture comprises rotating the closure component with respect to a longitudinal axis of the tubular member.

* * * * *